United States Patent [19]

Cleckner

[11] 4,096,661

[45] Jun. 27, 1978

[54] METHOD OF INCREASING THE GROWTH OF PLANTS GROWN FROM SEED

[76] Inventor: John Cleckner, 3414 Rustic Way La., Falls Church, Va. 22044

[21] Appl. No.: 773,985

[22] Filed: Mar. 3, 1977

[51] Int. Cl.² ............................................. A01N 7/00
[52] U.S. Cl. ........................................ 47/58; 71/77; 47/DIG. 10
[58] Field of Search ................ 47/58, DIG. 10; 71/77

[56] References Cited

U.S. PATENT DOCUMENTS 3,458,953  8/1969  Moses et al. .............................. 47/58

*Primary Examiner*—Robert E. Bagwill
*Attorney, Agent, or Firm*—Millen & White

[57] ABSTRACT

Improvement in one or more of germination time, germination rate, plant growth and crop yield of crops grown from seed in non-irrigated fields of fertile soil suitable for growing the crop, by applying a growth promoting amount of a linear alkylsulfonic acid surfactant, or non-phytotoxic salt thereof, only to the soil proximate the seeds proximate the time of planting.

18 Claims, No Drawings

METHOD OF INCREASING THE GROWTH OF PLANTS GROWN FROM SEED

BACKGROUND OF THE INVENTION

This invention relates to a method of increasing the growth of plants grown from seed by applying a surfactant to the soil in which they are grown.

The addition of surfactants to irrigation water or to water used to water plants to improve soil texture, to enhance water uptake by the soil or to obtain stimulation of growth of vegetation, has been known for over 25 years. See, e.g., U.S. Pat. Nos. 2,689,173; 2,778,809; 2,946,155; and 3,458,953. However, such usage of surfactants has not gained acceptance, at least in crop growing, for several reasons. First and foremost, some surfactants are known to be herbicides or toxic to plants, see, e.g., U.S. Pat. No. 2,531,276. They thus pose a threat to the crop. Some, especially the alkylbenzene sulfonates, resist biodegradation and persist in the soil, which is unacceptable under present environmental concepts. Others are known to be plant growth stimulants (U.S. Pat. Nos. 2,284,002 and 2,594,134) or plant growth regulators (3,713,804 and prior art cited therein). Such phytoactivity in a soil conditioner generally is considered a deterrent to its use because of its unpredictable effect upon crops subsequently planted in the soil. Also, the amount of surfactant required to significantly improve the texture of poor soil generally is too high to be economically attractive, particularly for use on large acreage; as is usual in the case of crops such as corn, wheat, etc. In addition, application procedures for some surfactants are time consuming or are not compatible with existing agricultural practices, e.g., surfactant must be thoroughly mixed with pulverized soil particles. Finally, one would not ordinarily use a soil conditioner on soil which already is satisfactory for growing crops. Thus, one or more of these considerations has limited, if not precluded, the use of surfactants in the manner contemplated in U.S. Pat. Nos. 2,689,173 and 2,946,195.

I have now found that favorable effects upon crops grown from seed can be economically achieved employing the specific surfactants and specific methods of application thereof according to the method of this invention.

SUMMARY OF THE INVENTION

In a process aspect, this invention relates to a method of growing crops from seed in non-irrigated fields in fertile soil suitable for growing the crop, which comprises applying only to that portion of the soil proximate the soil in which the seed is or is to be planted, during the period from about two weeks prior to planting to about six weeks after planting, a growth promoting amount of a linear alkyl sulfonic acid surfactant of at least 6 carbon atoms, or a non-phytotoxic salt thereof.

In a composition aspect, this invention relates to an aqeuous surfactant composition comprising 0.4-40% by weight of a mixture of surfactants consisting essentially of about 70% by weight of a linear alkylsulfonic acid surfactant of at least 6 carbon atoms, or a non-phytotoxic salt thereof, and about 30% by weight of a polyethoxylated linear alkanol nonionic surfactant.

In a second composition aspect, this invention relates to nitrogenous fertilizers comprising a mixture of surfactants as defined hereinabove.

In a third composition aspect, this invention relates to herbicides of the emulsifiable concentrate or surfactant compatible type comprising a mixture of surfactants as defined hereinabove.

Upon further study of the specification and appended claims, further objects and advantages of this invention will become apparent to those skilled in the art.

DETAILED DISCUSSION

This invention is based upon a surprising discovery that the application of the surfactants as defined herein to normal non-irrigated fields whose soil is fertile and already suitable for growing crops from seeds, proximate the time of planting the seeds, and proximate the location of the seeds in the soil, in amounts far below that required to significantly affect the overall texture of the soil in the field where the crop is grown, can significantly improve one or more of germination time, germination rate, rate of plant growth and crop yield.

The principle upon which these results are achieved appears to be a reduction in the energy required to release the water-soil particle bond of water physically bonded to the soil particles, thereby reducing the energy consumed by the growing plants in transferring the moisture from the soil into the plant structure and correspondingly increasing the proportion of plant energy available for root development, plant growth and crop yield. However, regardless of whether or not this is the mechanism by which the advantages of this invention are achieved, the result of practicing the method of this invention is a marked improvement in overall root development and plant growth and stamina. This result is particularly surprising in view of the fact that significant improvements can be achieved at surfactant application rates of as little as about 0.1 lb./acre. Quite obviously, therefore, the mechanism by which the advantages are realized is not due to an improvement of soil texture, which is achieved according to U.S. Pat. No. 2,689,173 by the application of alkylbenzenesulfonate surfactant at the rate of at least 10 lbs./acre and preferably 15-50 lbs./acre, and by the application of any surfactant and at the rate of about 22 lbs./acre, as taught by U.S. Pat. No. 2,946,155. Moreover, because the advantages are realized in non-irrigated fields, because of the relative short (about two weeks or less) life expectancy of the surfactants employed in the soil, and because of the timing of the application to the soil, these advantages cannot be attributed merely to more efficient adsorption of irrigation water into the soil which, according to U.S. Pat. No. 2,946,155, can be achieved at lower rates per acre by incorporating the surfactant in the irrigation water.

Any linear alkylsulfonic acid of at least 6 carbon atoms, or a non-phytotoxic salt thereof (LAS surfactant) can be employed. The term "surfactant" as used herein means a surface active agent which is effective in aqueous solutions, i.e. which lowers the surface tension of water. Those having not more than 20 carbon atoms, e.g., 8-18 carbon atoms, and mixtures thereof, are preferred. Their water soluble salts, e.g., alkali metal salts, preferably the sodium or potassium salts, are ordinarily employed although other salts, e.g., amine, calcium and magnesium, and the free acids can also be used, especially in soils having a pH above about 7.5 and when using low rates of application. The free acids can also be used in conjunction with ammonia fertilization to form the ammonium salts thereof. Sodium laurylsulfonate is especially preferred.

The LAS surfactants can be used alone or as a mixture with other non-phytotoxic surfactants, e.g., non-ionics. However, such mixtures generally give no better results and often give poor results than the LAS surfactant alone. A surprising exception are mixtures with nonionic surfactants whose solutions have lower surface tensions than the corresponding solutions of the same amount of LAS surfactant alone. Such a mixture is about a 70:30 by weight of sodium laurylsulfonate and a polyethoxylated linear alkanol. These are a well-known class of nonionic surfactants of the formula $CH_3(CH_2)_n—O—(CH_2CH_2O)_mH$, wherein $n$ is an integer from about 8–18, preferably about 11, and $m$ is an integer having an average value of at least about 8–20, e.g., about 12. They are generally commercially available as a mixture having a varying number of ethoxy groups. Ethoxolated lauryl alcohol having an average of about 12 ethoxy groups is especially suitable.

The amount of LAS surfactant which needs to be applied to achieve one or more improved germination time, germination rate, growth rate and crop yield is surprisingly low, e.g., as little as 0.05 lbs./acre. Generally, about 0.1–5 lbs./acre is applied. Under particularly adverse conditions of soil quality and moisture content, higher amounts, e.g., up to about 10 lbs./acre, may sometimes be required but this is not usually the case. Although even larger amounts can be applied, they usually serve no useful purpose. Preferably, about 0.5–2 lbs./acre is applied.

The LAS surfactant is conveniently applied as an aqueous solution, e.g., 0.4–40% by weight, the concentration being determined partially by the available equipment and the rate of application. At low rates of application, e.g., up to 2 lbs/acre, about 1.25% solution is often convenient because 20 gallons at most of solution per acre is required. At higher application rates, e.g., 5 to 10 lbs/acre, more concentrated solutions are sometimes more convenient. The LAS surfactant can also be applied in admixture with a liquid fertilizer or surfactant compatible herbicides.

The LAS surfactant can also be applied in solid form, either as much or in admixture with a solid carrier, e.g., a solid fertilizer. When applied in solid form or as a concentrated solution, greater care should be taken to avoid making direct contact with the seeds because although the LAS surfactants are non-phytotoxic, like most chemicals, they can manifest a toxic effect in direct contact in high concentrations with the seeds or growing plants.

A unique feature of the process of this invention is that the LAS surfactant need not be applied to all of the soil in the field, because its function is not to significantly alter the texture of the soil and thereby enhance water adsorption during or after irrigation, or promote leaching of salts therefrom, as in the process of U.S. Pat. No. 2,946,155. Therefore, it need be applied only to some or all of that portion of the solid which is proximate, i.e., within about six inches, of the seeds. Application beyond that distance serves no useful purpose, since the LAS surfactant biodegrades before the plant roots can reach it or before it can migrate near enough to the seeds or the plants grown therefrom to exercise its beneficial effects. Moreover, it is unneccessarily wasteful of the surfactant and defeats the prime objective of this invention, viz., achieving one or more of the advantages set forth hereinabove in an economically feasible manner. Thus, by the method of this invention, advantageous effects upon plant growth and crop yield can be achieved with far less surfactant than heretofore employed to alter the texture of the soil in the field.

Preferably, the LAS surfactant is applied in an area apaced apart at a distance from the seeds, e.g., of about 0.5–4 inches, preferably about 1–2 inches, usually as a thin strip or in a thin line parallel to a row of seeds. It is not necessary that the LAS surfactant be distributed evenly on or in the soil proximate the seeds. Thus, a 0.25–0.5 inch wide continuous line of a concentrated solution, e.g., 40%, of the LAS applied to the surface of the soil parallel to a line of the seeds and about 1 inch therefrom is about as effective as a wider strip of a more dilute solution thereof, e.g., about 10%, applied 1–2 inches therefrom and worked into the top 2–6 inches of soil.

Although the surfactant is preferably applied to the soil proximate but spaced apart from the seeds, with seeds less sensitive to chemicals, e.g., those with hard seed coats, such as corn, and especially with dilute solutions, e.g., 10% or less, the surfactant solution can be applied directly to the soil in which the seeds are or are to be planted.

The LAS surfactant is applied within the period beginning about 2 weeks prior to planting and ending about 6 weeks after planting, preferably within 1 week prior to or one week after, more preferably, withhin a day of planting, and most preferably, concurrently with planting. Although best results are obtained when the LAS surfactant is applied concurrently with planting or within a day or two before or after, advantages are also achieved if the LAS surfactant is applied at any time prior to planting up to the biodegradation time for the LAS surfactant in the soil under the conditions existing at the time it is applied thereto, which usually is within about 2 weeks prior to planting, and any time thereafter up to the time after germination when the root structure for the mature plant has been largely determined, which usually is within about 6 weeks after planting for most plants. Application concurrently with or prior to planting will achieve most or all the advantages of this invention whereas application a substantial period after planting will generally achieve only enhanced growth rate.

In a preferred embodiment of this invention, the initial application of LAS surfactant is followed by one or more subsequent applications thereof in the same manner, each spaced apart from each other by about 10–30 days. Because it often is not economically feasible to apply the surfactant in a separate operation, such subsequent applications are usually combined with another operation necesitated by the nature of crop, e.g., weeding or working the soil, spraying with insecticide, fertilization, etc. Generally the last application of surfactant should be prior to flowering or tasseling, unless the plant itself rather than its fruit or seed, is the intended crop, e.g., corn for silage. In these applications as in the first application, because of the nature of the mechanism by which the advantages of the invention are achieved, the LAS surfactant is applied only to the soil proximate the growing plant. Applying it directly to the plant is generally undesirable and applying it to other areas of the soil is wasteful.

The method of this invention can be practiced in any fertile soil suitable in untreated form for growing the intended crop, including heavy clay soil, highly humus soil, loam, sand, and even synthetic soil, e.g., vermiculite. The more moisture in the soil that is unavailable to the crop, the more spectacular are the results achieved with the method of this invention. Even in rich, highly fertilized soil, very significant improvements in the crops are realized.

As stated hereinbefore, the only soil to which the surfactants employed in the process of this invention need be applied is that within about 6 inches of the seeds. The remaining soil in the field can remain untreated and is essentially unaffected by the treatment.

The method of this invention can be employed with any crop from seed, i.e., both monocotyledoneae and dicotyledoneae. This fact renders highly unlikely the possibility that the surfactants act via a plant growth hormone mechanism. The monocotyledoneae are preferred, especially the edible grains and most especially corn.

Examples of crops which are improved by the method of this invention are the grasses, sugar cane and beets, alfalfa, the legumes, e.g., soybeans, black beans, the edible grains, corn, both silage and field corn, wheat, barley, oats, cotton, tobacco, and the truck farming crops, e.g., lettuce, tomatoes, radishes, sweet peas, string beans, cucumbers, celery, carrots, cabbage, etc. A particular advantage can be achieved with the latter crops, the whole field of which is harvested only once, e.g., tomatoes, in that more uniform maturity throughout the whole field can be achieved, an advantage of substantial economic significance.

To achieve more uniform crop maturity throughout the field, usually an application rate of about 3–5 lbs/acre is employed.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

The following are the results of test applications of dilute aqueous solutions (5–14%) of a 70:30% by weight mixture of sodium laurylsulfonate and polyethoxylated (Av. 12) lauryl alcohol. (Union Carbide "Tergitol 15-S-12")

A: Corn

| Conditions: | Fertilizer (per acre): |
|---|---|
| Soil : Sandy | 600 lbs. 4-8-16 |
| Seeds : 14,500/acre | 100 lbs. $NH_4NO_3$ (side dressing) |
| Rainfall : 19.7 inches | 18 lbs. FTE 503 (trace elements) |
| Growth Time : Full Season | 200 lbs. $NH_4NO_3$ (when plants were 2 ft. tall) |

| Treatment | No. of Test Plots (48ft.$^2$) | Corn Yield (lbs./plot) | % Change from Control |
|---|---|---|---|
| Control | 16 | 7.08 | — |
| Surfactant-1 qt./acre | 16 | 8.69 | +23% |
| Surfactant-2 qts./acre | 16 | 8.74 | +23% |
| Control | 3 | 5.43 | — |
| Surfactant-32 qts./acre | 4 | 6.84 | +26% |

B: Corn

| Conditions: | Fertilizer: |
|---|---|
| Soil : Clay | 186 lbs. nitrogen (N) |
| Seeds : 26,000/acre | 72 lbs. phosphate ($P_2O_5$) |
| Rainfall : 12.6 inches | 100 lbs. potash ($K_2O$) |
| Growth Time : Full Season | |

| Treatment | No. of Test Plots (62ft.$^2$) | No. of Bushels of corn/acre | % Change over Control |
|---|---|---|---|
| Control | 7 | 97 | — |
| Surfactant | 5 | 142 | +46% |

C: Corn

| Conditions | Treatment | No. of Test Plots (1.5ft.$^2$) | 16-day 5-plant wt.(g.) | % Change over Control |
|---|---|---|---|---|
| Soil: Potting | Control | 1 | 2.5 | — |
| Seeds: 20/plot | Surfactant (1 qt./acre) | 2 | 3.5 | +40% |
| Water: 1oz./plot | | | | |

D: Corn

| Conditions | Treatment | No. of Test Plots (1.5ft.$^2$) | No. of Plants Sprouted (16 days) | % Change over Control |
|---|---|---|---|---|
| Soil: Potting | Control | 1 | 6 | — |
| Seeds: 100/plot | Surfactant 1 qt./acre | 1 | 10 | + 67% |
| Water: 5oz./plot | Surfactant 1 qt./acre | 1 | 12 | +100% |
| | Surfactant 100:0 | 1 qt./acre LAS:EO | 1 | 18 | +300% |
| | Surfactant 90:10 | 1 qt./acre LAS:EO | 1 | 7 | + 17% |
| | Surfactant 80:20 | 1 qt./acre LAS:EO | 1 | 6 | 0% |
| | Surfactant 60:40 | 1 qt./acre LAS:EO | 1 | 6 | 0% |
| | Surfactant 50:50 | 1 qt./acre LAS:EO | 1 | 4 | − 33% |
| | Surfactant 30:70 | 1 qt./acre LAS:EO | 1 | 8 | + 25% |
| | Surfactant 0:100 | 1 qt./acre LAS:EO | 1 | 5 | − 17% |

E: Corn

| Conditions: | |
|---|---|
| Soil : Loam | |
| Water : 84 oz./plot | |

| Treatment | No. of Plots (0.75ft$^2$) | Averge days to Germination | % Change over Control | 16-day 5-plant wt. (g.) | % Change over Control |
|---|---|---|---|---|---|
| Control | 21 | 5.26 | — | 4.44 | — |
| Surfactant 1/14 qt./acre | 20 | 4.23 | −20% | 5.47 | +23% |
| Surfactant 1 qt./acre | 21 | 4.48 | −15% | 5.61 | +26% |
| Surfactant 6 qt./acre* | 19 | 5.67 | + 8% | 4.17 | − 6% |

*applied at a concentration 20 times that of other applications

F: Corn

| Conditions | Treatment | No. of Test Plots (1.25 ft.²) | 16-day Ave. 5-plant wt. (g.) | % Change over Control |
|---|---|---|---|---|
| Soil : Potting | Control | 1 | 3.1 | — |
| Seeds : 20/plot | Surfactant 1/10qt/acre | 2 | 3.8 | +23% |
| Water : 32oz/plot | | | | |
| | Surfactant 1 qt/acre | 2 | 4.6 | +48% |
| Surfactant 100% | 1 qt/acre LAS | 1 | 4.1 | +32% |

G: Corn

Conditions
Soil : Potting
Seeds : 20/plot
Water : 1.25 liters/plot

| Treatment | No. of Test Plots (1.25ft.²) | No. of Plants sprouted (16 days) | % Change over Control | Wt. of Sprouted Plants | % Change over Control |
|---|---|---|---|---|---|
| Control | 1 | 14 | — | 4.8 | — |
| Surfactant 1 qt/acre | 1 | 19 | +36% | 9.5 | +98% |

H: Corn

Conditions
Soil : Potting
Water : 1.425 liters

| Treatment | No. of Plots 1.5 ft.² | 16-day 5 Plant Weight (g) | % Change Over Control |
|---|---|---|---|
| Control | 1 | 5.9 | — |
| Surfactant 1 qt/acre 100% LAS | 1 | 7.3 | +24% |
| Surfactant 1 qt/acre 100% EO | 1 | 3.0 | −49% |
| Surfactant 1 qt/acre 25:75 LAS:EO | 1 | 3.0 | −47% |

I: Radishes

| Conditions | Treatment | No. of Test Plots (1.25ft²) | 16-day 10-plant wt. (g.) | % Change over Control |
|---|---|---|---|---|
| Soil : Potting | Control | 1 | 0.2 | — |
| Seeds : several 100/plot | Surfactant 1 qt/acre | 1 | 0.7 | +250% |
| Water : 1.25 liters/plot | | | | |
| | Surfactant 1 qt/acre | 2 | — | — |

J: Rye Grass

Conditions
Soil : Potting
Seeds : 50/plot (Petri Dish)
Water : 3 applications of 0.25 in.

| Treatment | Days until first Germination | % Change over Control | Plants Sprouted (16 days) | % Change over Control | Longest Stem (in.) | % Change over Control |
|---|---|---|---|---|---|---|
| Control | 8 | — | 6 | — | 0.4 | — |
| Surfactant 1 qt./acre | 5 | −38% | 10 | +67% | 1.5 | +275% |

K: Tomato

Conditions
Soil : Potting
Seeds : several 100/acre
Water : 1.25 liters/plot

| Treatment | No. of Test Plots (1.25ft.²) | 16-day 20-Plant wt. (g.) | % Change over Control |
|---|---|---|---|
| Control | 1 | 0.8 | — |
| Surfactant 1 qt./acre | 1 | 1.0 | +38% |

L: Black Beans

Conditions
Soil : Potting
Seeds : 9/Plot

| Treatment | No. of Test Plots (1. ft.²) | Ave. Germination Time | % Change Over Control | Ave. Germination Rate | % Change Over Control |
|---|---|---|---|---|---|
| Control | 5 | 9.55 days | — | 22% | — |
| Surfactant 1 qt./acre | 5 | 7.79 days | −18% | 42% | +90% |

| | 16-day Total Plant Wt. (g) | % Change Over Control | 16-day Total Leaf Wt. | % Change Over Control |
|---|---|---|---|---|
| Control | 23.4 | — | 5.7 | — |
| Surfactant 1 qt./acre | 41.3 | +76% | 13.1 | +130% |

[Soybeans can be treated in substantially the same manner.]

M: Herbicidal Formulations

Surfactant — Same as in prior examples — about 0.5 to 2 qts./pref. 1 qt./acre.

Atrazine (2-chloro-4-ethylamino-6-isopropylamino-5-triazine) — about 0.5 to 4, preferably 1 lb/acre.

The above active ingredients to be applied as an aqueous dispersion 0.4–10% by weight, the concentration being determined by the available equipment and applied to the soil proximate to the seeds, e.g., 0.5–6 inches. The period of application is within two weeks prior to planting and ending about 6 weeks after planting, preferably within one week prior to, or one week after, more preferably within a day of planting, and most preferably concurrently with the planting.

Other herbicides which can be substituted for atrazine in the above formulation are surfactant-compatible herbicides, other exemplary materials, which include but are not limited to simazin, Bladex and Cobex.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a method of growing crops from seed in non-irrigated fields in fertile soil suitable for growing the crop, the improvement which comprises applying only to that portion of the soil proximate the soil in which the seed is or is to be planted, during the period from about two weeks prior to planting to about six weeks after planting, a growth promoting amount of a linear alkyl sulfonic acid surfactant of at least 6 carbon atoms, or a non-phytotoxic salt thereof.

2. A method according to claim 1, wherein the surfactant is applied concurrently with planting.

3. A method according to claim 1, wherein the surfactant is applied as a 0.4–40% aqueous solution.

4. A method according to claim 1, wherein the surfactant is applied at a distance of about 0.5–6 inches from the seeds.

5. A method according to claim 1, wherein the surfactant is an alkali metal salt of a $C_8$–$C_{18}$ linear alkylsulfonate.

6. A method according to claim 1, wherein the surfactant is sodium laurylsulfonate.

7. A method according to claim 1, wherein the surfactant is about a 70:30 by weight mixture of sodium laurylsulfonate and a linear nonionic detergent.

8. A method according to claim 1, wherein the surfactant is applied at a rate of about 0.5–2 lbs./acre.

9. A method according to claim 1, wherein the surfactant is applied to the soil in the same manner at least once again during the period at ten days after the first application but before the crop reaches flowering or tasseling.

10. A method according to claim 1, wherein the seeds are monocotyledoneae.

11. A method according to claim 1, wherein the seeds are gramineae.

12. A method according to claim 1, wherein the seeds are corn.

13. A method according to claim 1, wherein the surfactant is applied concurrently with planting as a 0.4–40% aqueous solution at a rate of about 0.5–2 lbs./acre.

14. A method according to claim 13, wherein the surfactant is applied at a distance of about 0.5–6 inches from the seeds.

15. A method according to claim 13, wherein the surfactant is sodium laurylsulfonate.

16. A method according to claim 13, wherein the seeds are dicotyledoneae.

17. A method according to claim 13, wherein the seeds are leguminosae.

18. A method according to claim 13, wherein the seeds are soybeans.